(12) United States Patent
Thevenier et al.

(10) Patent No.: US 11,533,941 B2
(45) Date of Patent: Dec. 27, 2022

(54) FERMENTED NUTRITIONAL COMPOSITION FOR COW'S MILK PROTEIN ALLERGIC SUBJECTS

(71) Applicant: NESTEC S.A., Vevey (CH)

(72) Inventors: Anne Thevenier, Bern (CH); Susanne Schuh, Gumlingen (CH); Katja Johnson, Konolfingen (CH); Martin Vikas, Oberdiessbach (CH); Martinas Kuslys, Grosshoechstetten (CH); Rinat Ran-Ressler, Bridgewater, NJ (US); Koraljka Rade-Kukic, Lafayette, CA (US)

(73) Assignee: Societe des Produits Nestle S.A., Vevey (CH)

( * ) Notice: Subject to any disclaimer, the term of this patent is extended or adjusted under 35 U.S.C. 154(b) by 699 days.

(21) Appl. No.: 16/331,589

(22) PCT Filed: Sep. 13, 2017

(86) PCT No.: PCT/EP2017/073046
§ 371 (c)(1),
(2) Date: Mar. 8, 2019

(87) PCT Pub. No.: WO2018/050710
PCT Pub. Date: Mar. 22, 2018

(65) Prior Publication Data
US 2019/0246680 A1    Aug. 15, 2019

Related U.S. Application Data

(60) Provisional application No. 62/393,790, filed on Sep. 13, 2016.

(51) Int. Cl.
*A23L 33/185* (2016.01)
*A23L 33/00* (2016.01)
(Continued)

(52) U.S. Cl.
CPC ............ *A23L 33/185* (2016.08); *A23C 11/06* (2013.01); *A23L 33/115* (2016.08); *A23L 33/135* (2016.08);
(Continued)

(58) Field of Classification Search
CPC ........ A23L 33/135; A23L 33/40; A23L 11/06; A23V 2002/00; A23V 2250/548; A23Y 2240/75; A23Y 2300/55
(Continued)

(56) References Cited

U.S. PATENT DOCUMENTS 7,160,564 B2 * 1/2007 Triantafyllou Oste .................... A23C 11/10
426/52
8,859,029 B2 10/2014 Weenen et al.
(Continued)

FOREIGN PATENT DOCUMENTS

| CN | 104017739 | 3/2014 |
| CN | 104017739 | 9/2014 |

(Continued)

OTHER PUBLICATIONS

Chouraqui et al. "Acidified Milk Formula Supplemented With Bifidobacterium lactis: Impact on Infant Diarrhea in Residential Care Settings" Journal of Pediatric Gastroenterology and Nutrition, 2004, vol. 38, pp. 288-292.
(Continued)

*Primary Examiner* — Hamid R Badr
(74) *Attorney, Agent, or Firm* — K&L Gates LLP

(57) ABSTRACT

A nutritional composition obtainable by fermenting a mixture comprising protein, carbohydrate and fat, wherein the major source of protein is potato protein, and wherein the mixture is fermented by lactic acid-producing bacteria.

17 Claims, 9 Drawing Sheets

(51) Int. Cl.
  A23L 33/135    (2016.01)
  A23C 11/06     (2006.01)
  A23L 33/115    (2016.01)
  A23L 19/12     (2016.01)
  A23C 9/123     (2006.01)
(52) U.S. Cl.
  CPC ............ *A23L 33/40* (2016.08); *A23C 9/1238* (2013.01); *A23L 19/12* (2016.08); *A23V 2002/00* (2013.01); *A23V 2200/00* (2013.01); *A23V 2200/304* (2013.01); *A23V 2200/3204* (2013.01); *A23V 2250/548* (2013.01); *A23Y 2220/43* (2013.01); *A23Y 2220/49* (2013.01); *A23Y 2220/63* (2013.01); *A23Y 2220/73* (2013.01); *A23Y 2240/41* (2013.01); *A23Y 2240/65* (2013.01); *A23Y 2240/75* (2013.01); *A23Y 2300/49* (2013.01); *A23Y 2300/55* (2013.01)
(58) Field of Classification Search
  USPC .......................................................... 426/42
  See application file for complete search history.

(56) References Cited

U.S. PATENT DOCUMENTS

| | | | |
|---|---|---|---|
| 9,596,876 | B2 | 3/2017 | Boehm et al. |
| 10,986,848 | B2 | 4/2021 | Holz-Schietinger et al. |
| 2004/0146600 | A1 | 7/2004 | Schlothauer et al. |
| 2010/0003394 | A1 | 1/2010 | Giuseppin et al. |
| 2010/0247710 | A1 | 9/2010 | Giuseppin et al. |
| 2010/0330040 | A1 | 12/2010 | Knol et al. |
| 2013/0337105 | A1 | 12/2013 | Ludwig et al. |
| 2015/0033453 | A1 | 2/2015 | Hageman |
| 2015/0164113 | A1 | 6/2015 | Moroni et al. |
| 2015/0305359 | A1 | 10/2015 | Ao et al. |

FOREIGN PATENT DOCUMENTS

| | | |
|---|---|---|
| CN | 105265746 | 1/2016 |
| DE | 10359316 | 7/2005 |
| DE | 10359316 A1 | 7/2005 |
| EP | 2380446 | 10/2011 |
| EP | 2695522 | 2/2014 |
| EP | 2695522 A1 | 2/2014 |
| RU | 2075941 | 3/1997 |
| SE | 1050965 | 1/2012 |
| SE | 1050965 A1 | 1/2012 |
| WO | 9742834 | 11/1997 |
| WO | 0237984 | 5/2002 |
| WO | 2004105508 A1 | 12/2004 |
| WO | 2094105508 | 12/2004 |
| WO | 2008069650 | 6/2008 |
| WO | 2009065905 | 5/2009 |
| WO | 2009067000 | 5/2009 |
| WO | 2011121379 | 10/2011 |
| WO | 2011121379 A1 | 10/2011 |
| WO | 2012078046 | 6/2012 |
| WO | 2013062402 | 5/2013 |
| WO | 2014110540 | 7/2014 |
| WO | 2014174149 | 10/2014 |
| WO | 2014174149 A1 | 10/2014 |
| WO | 2015164020 | 10/2015 |
| WO | 2015170985 | 11/2015 |
| WO | 2015187817 | 12/2015 |
| WO | 2016133448 | 8/2016 |

OTHER PUBLICATIONS

Liang et al. "Chemical and Thermal Characterization of Potato Peel Waste and Its Fermentation Residue as Potential Resources of Biofuel and Bioproducts Production" Journal of Agricultural and Food Chemistry, 2014, vol. 62, pp. 8421-8429.

Walstra et al., "Dairy Science and Technology", Second Edition, 2006, 48 Pages.
"DairinQ Leaflet", 2009, 2 Pages.
"Solanic Folder on Food Fortification and Application in Dairy-Free Milk", Solanic 100—No. 1 Plant Protein for Nutrition, 2014, pp. 1-4.
"Dairy-Free Milk Drink with Solanic Potato Protein", 2015, 2 Pages.
"Dietary Protein Quality Evaluation in Human Nutrition", FAQ Food and Nutrition Paper 92, 2013, pp. 1-66.
Pope, "Fermented Potatoes Recipe", The Healthy Home Economist, 2010, 17 Pages.
Kutshik et al., "Protein Enrichment of Irish Potatoes by Fermentation Process Using Mutant Isolates of Lactobacillus Bulgaricus", International Journal of Biological and Chemical Sciences, vol. 4, Issue No. 6, 2010, pp. 1898-1904.
Gemechu., "Review on Lactic Acid Producing Bacteria Function in Milk Fermentation and Preservation", African Journal of Food Science, vol. 9, Issue No. 4, 2015, pp. 170-175.
Zourari et al., "Metabolism and Biochemical Characteristics of Yogurt Bacteria. A Review", vol. 72, Issue No. 1, 1992, pp. 1-34.
"NEVO-online", National Institute for Health and Environment, Retrieved from (https://nevo-online.rivm.nl/.), Aug. 6, 2021, pp. 1-4.
"Experimental Report on Fermented Potatoes", Aug. 31, 2021, pp. 1-3.
Bernat et al., "Probiotic Fermented Almond "Milk" as an Alternative to Cow-Milk Yoghurt", International Journal of Food Studies, vol. 4, 2015, pp. 201-211.
Ladokun et al., "Fermented Milk Products from Different Milk Types", Food and Nutrition Sciences, vol. 5, 2014, pp. 1228-1233.
Rao et al., "Technical Note: Preparation of a Yogurt-Like Product from Cowpeas and Mung Beans", International Journal of Food Science and Technology, vol. 23, 1988, pp. 195-198.
Pszczola, "Plugging Into Proteins", Food Technology, 2013, pp. 54-64.
"Commission Delegated Regulation (EU) 2016/127", Official Journal of the European Union, Sep. 25, 2015, 29 Pages.
"Functional Ingredients For Food", Danisco Product Guide (Selected Pages), 8 Pages.
Shin et al., "Preparation of Yogurt Added with Potato and its Characteristics", Korean Journal of Food Science and Technology, vol. 26, Issue No. 3, 1994, pp. 266-271, (English Translation Submitted).
Mital et al., "Fermentation of Soy Milk by Lactic Acid Bacteria. A Review.", Journal of Food Protection, vol. 42, Issue No. 11, 1979, pp. 895-899.
Seppala, "Characterization of Potato Allergens", 2001, 70 Pages.
Beausoleil et al., "Anaphylaxis to Raw Potato", Annals of Allergy, Asthma & Immunology, vol. 86, Issue No. 1, 2001, pp. 68-70.
Castells et al., "Allergy to White Potato", Journal of Allergy and Clinical Immunology, vol. 78, Issue No. 6, 1986, pp. 1110-1114.
Tamime, "Fermented Milks", 2006, 16 Pages.
"Codex Standard for Fermented Milks", Codex Stan 243-2003, pp. 1-8.
"Dairy-Free Foods"—Avebe, Retrieved from (https://web.archive.org/web/20160323084237/https://www.avebe.com/dairy-free-foods/), Jun. 23, 2016, pp. 1-3.
Lokra et al., "Industrial Proteins from Potato Juice. A Review", Food, vol. 3, issue No. 1, 2009, pp. 88-95.
"Maize Stover"—Feedipedia, Retrieved from (https://web.archive.org/web/20160811115512/https://www.feedipedia.org/node/16072), Aug. 11, 2016, pp. 1-4.
"Sorghum, Sweet, Aerial Part, Silage",—Feedipedia, Retrieved from (https://web.archive.org/web/20161031005421/https://www.feedipedia.org/node/12683), Oct. 31, 2016, pp. 1-3.
"Potato",—Wikipedia, Retrieved from (https://web.archive.org/web/20160829031614/https://en.wikipedia.org/wiki/Potato), Aug. 29, 2016, pp. 1-13.
"Milk Facts", Retrieved from (https://web.archive.org/web/20160816082144/http://www.milkfacts.info/Milk Processing/Yogurt Production.htm), Aug. 16, 2016, pp. 1-3.

(56) References Cited

OTHER PUBLICATIONS

DairinQ; Soianic high performance ingredients: www.solanic.eu.
Walstra Pieter et al., "Dairy Science and Technology" 2006: Taylor & Francis Group, LLC.
Avebe, "No. 1 Plant Protein for Nutrition" Pure Free From Sustainable Potato Protein, Avebe U.A.
Avebe, "Dairy-Free Milk Drink with Soianic Potato Protein", Avebe U.A.
Auckland, New Zealand "Dietary protein quality evaluation in human nutrition" Mar. 31-Apr. 2, 2011.
Pope Sara, "Fermented Potatoes Recipe,"the healthy home economist: https://www.thehealthyhomeeconomist.comfauthor/sarah/.
Kutshik, J.R., "Protein enrichment of Irish potatoes by fermentation process using mutant isolates of Latobacillus bulgaricus" Department of Biochemistry, Int. J. Biol. Chem. Sci. 6(6): 1898-1904, Dec. 2010.
Gemechu Teshome, "Review on lactic acid bacteria function in milk fermentation and preservation," Deparment of Animal Science, College of Agriculture and Natural Resources, Mizan-Tep University, Received Feb. 3, 2015.
Zourari A, "Metabolism and biochemical characteristics of yogurt bacteria. A review" (Received Jul. 5, 1991; accepted Oct. 1, 1991).
NEVO-online versie 2019/6.0.
Vlaanderen Jerome, "Experimental report" Avebe; Aug. 31, 2021. FIELD dairy industry.
Bernat Neus et al., "Probiotic fermented almond "milk" as an alternative to cow-milk yoghurt" Received: Jul. 17, 2014; Published online: Oct. 18, 2015.
Ladokun Olusola et al, "Fermented Milk Products from Different Milk Types," Department of Biochemistry, Lead City University; Received Apr. 20, 2014; revised May 29, 2004; accepted Jun. 8, 2014.
D.R. Rao, S.R. Pulusano, "Technical note: Preparation of a yogurt-like product from cowpeas and mung beans" International Journal of Food Science and Technology (1988) 23, 195-198.
Pszczola Donald, "Plugging into Proteins" foodtechnology; www.ift.org.
"Functional ingredients for food" Danisco A/S.
Commission Delegated Regulation (EU) 2016/127 of Sep. 25, 2015.
Milk Facts "Nutrient Content of Milk Varieties".
Commission Directive 2006/141/EC of Dec. 22, 2006 on infant formulae and follow-on formulae and amending Directive 1999/21/EC.
Seppala Ulla, MSc et al., "Identification of patatin as a novel allergen for children with positive skin prick test responses to raw potato," Helsinki and Tampere, Finland; Copyright; 1999.
U. Sepapala et al. "Identification of four novel potato (*Solanum tubersosum*) allergens belonging to the family of soybean trypsin inhibitors"; Institute of Biotechnology University of Helsinki; Feb. 1, 2001.
Standard for Infant Formula and Forumulas for Special Medical Purposes Intended Infants: Codex Stan 72-1981.
National Intellectual Property Administration, PRC Appication publication No. CN 104017739, Sep. 3, 2014.
Liang Shaobo et al, "Chemical and Thermal Characterization of Potato Peel Waste and Its Fermentation Residue as a Potential Resources for Biofuel and Bioproducts Production" Environmental Science Program; J. Agric. Food Chem. 2014, 62, 8421-8429.
Shin Yong-Seo et al, "Preparation of Yogurt Added with Potato and its Characteristics" Department of Agricultural Chemistry; vol. 26, No. 3, pp. 266-271 (1994).
B.K. Mital et al. "Fermentation of Soy Milk by Lactid Acid Bacteria. A Review" Department of Food Science and Technology (Received for publication Feb. 26, 1979).
Seppala Ulla, "Charazterization of Potato Allergens" National Public Health Institute; Mar. 9, 2011; Helsinki 2001.
Beausoleil Janet, MD, et al, "Anaphylaxis to raw potato" Annals of Allergy, Asthma, & Immunology.
M, C, Castells, MD et al, "Allergy to white potato" D12.
Tamime A.Y "Fermented Milks" Society of Dairy Technology; 2006.
Codex Standard for Fermented Milks, Codex Stan 243-2003.
Avebe: Diary Free Foods https://web.archive.org/web/2016032308423 7//https://www.avebe.com/dairy-free-foods//.
Lokra Sissel et al., "Industrial Poteins from Potato Juice. A Review." Food, 2009 Global Science Books.
Maize stove—Feedipedia, Jul. 7, 2021 D18.
Sorghum, sweet, aerial part, silage—Feedipedia, Jul. 7, 2021 D19.
"Potato" Wikipedia https://web.archive.org/web/20160829031614/https:/en.wikipedia.org/wiki/Potato.
Milk Facts; https://web.archive.org/web/20160816082144/http://www.milkfacts.info/Milk Processing/Yogurt Production.htm.
English Translation of SE1050965A1.
Zhang et al., "Nutrition Value Evaluation of Potato Protein", Food Science and Technology, vol. 11, Nov. 20, 2007, pp. 219-221.
Fan et al., "Development and Existing Problems of Soy-Based Infant Formula", Science and Technology of Food Industry, vol. 34, Issue No. 3, Feb. 1, 2013, pp. 365-369, 374.
Ding et al.,"Quality and Quantity of Proteins and the Health of Children", Chinese Journal of Practical Pediatrics, vol. 30, Issue No. 12, Dec. 6, 2015, pp. 884-889.
Zhang et al., "Research and Development of Compound Rice Nutritional Powder", Cereals and Oils Processing, vol. 9, Aug. 8, 2006, pp. 81-83.
China Patent Office Action for Application No. 201980000287.9, dated Mar. 2, 2022, 15 Pages.
Zhang Ze-sheng et al., "Nutrition value evaluation of potato protein" Tianjin Key-Laboratory of Food Nutrution and Safety; Tianjin University of Science and Technology, Tianjin 300457.
Chinese Office Action for Chinese Appl No. 20198000287.9 dated Mar. 2, 2022.
English translation of Chinese Office Action for Chinese Appl No. 20198000287.9 dated Mar. 2, 2022.

\* cited by examiner

FERMENTED NUTRITIONAL COMPOSITION FOR COW'S MILK PROTEIN ALLERGIC SUBJECTS

CROSS REFERENCE TO RELATED APPLICATIONS

The present application is a National Stage of International Application No. PCT/EP2017/073046, filed on Sep. 13, 2017, which claims priority to U.S. Provisional Application No. 62/393,790, filed on Sep. 13, 2016, the entire contents of which are being incorporated herein by reference.

FIELD OF THE INVENTION

The present invention relates to nutritional compositions. In particular, the invention relates to infant formulas that are suitable for subjects with cow's milk protein allergy.

BACKGROUND TO THE INVENTION

Human breast milk and breast feeding are considered to be the optimal form of nutrition for healthy infants during the first months of life. However, there is a need for nutritional sources that can be used in addition to breast milk. Furthermore, not all infants can be breast fed and the needs of more vulnerable infants, such as preterm infants, cannot be achieved by their mother's milk, so there is also a need for alternatives to breast milk.

Nutritional compositions that satisfy the nutritional requirements of infants may be used as a substitute for or complement to human breast milk. Preferably, infant formulas should have an acceptable taste, and be hypoallergenic when targeted to infants who are allergic or at risk of allergy.

Infant formulas are typically formulated with cow's milk protein. For example, bovine whey protein and/or casein are often used as the protein source in infant formulas. However, some infants exhibit an allergy to cow's milk proteins, making such formulas unsuitable. Allergies to cows' milk and to infant formulas containing cow's milk protein may be due to the differences between the proteins in cows' milk and those in human milk. The principal recognised cow's milk allergens are alpha-lactalbumin (aLA), beta-lactoglobulin (bLG) and bovine serum albumin (BSA).

To reduce allergenicity, cow's milk proteins may be hydrolysed (e.g. enzymatically) either partially, or in the case of products intended for the management of Cow's Milk Protein Allergy (CMPA), extensively. However, such proteins must be highly processed to provide sufficient hydrolysis to reduce the risk of an allergic reaction. Such processing may be viewed unfavorably with an increasing tendency to provide more natural diets and a strong hydrolysis process also tends to have a negative impact on taste. In addition, the extensive processing increases the cost of the product formulas.

Alternatives to cow's milk protein may be used in nutritional compositions, for example soy and rice proteins. However, soy-based nutritional compositions are not recommended by the European Society for Paediatric Gastroenterology, Hepatology and Nutrition (ESPGHAN) for infants (0-12 months), because of the risk of a cross allergic response. Rice-based nutritional compositions require the addition of numerous free amino acids to provide the correct amino acid profile for infant formulas, due to the incomplete natural amino acid distribution in rice proteins. This increases cost and may provide the resulting formula with a less palatable taste. Furthermore, rice proteins are generally insoluble and require at least partial hydrolysis for solubilisation.

Infant formulas may be formulated entirely from free amino acids for infants with severe cases of multiple allergies. However, ESPGHAN guidelines indicate that such formulas should not be used as a first line solution in the case of cow's milk protein allergic infants. Furthermore, over-prescription of amino acid based formulas adds to the cost burden on national health systems as amino acid based formulas are even more expensive than extensively hydrolysed formulas.

Accordingly, there is a significant need for nutritional compositions, such as infant formulas, that comprise less potential allergens, and preferably which require minimal processing, have good taste and have low cost. In particular, there is a need for nutritional compositions, such as infant formulas, that are suitable for administration to subjects with cow's milk protein allergy.

SUMMARY OF THE INVENTION

The inventors have developed a fermented nutritional composition based on potato protein as the major protein source, which is naturally absent in the major allergens found in milk and soy. Accordingly, the nutritional composition may provide a naturally hypoallergenic infant formula or nutritional product (e.g. yoghurt-like product) that is suitable for subjects with cow's milk protein allergy.

In particular, the inventors have found that it is possible to successfully ferment a nutritional composition base (e.g. an infant formula base) comprising potato protein as the major protein source. Depending on the particular potato protein source used, the product structure achieved can be tailored to be more pudding-like (e.g. using a high molecular mass potato protein fraction, such as greater than 35 kDa) or quite liquid (e.g. using a low molecular mass potato protein fraction, such as less than 35 kDa). Furthermore, depending on the length of fermentation and strain used, different tastes can be achieved.

The fermented nutritional compositions may have an acidic pH, which provides improvement in food safety, in particular in locations where improper water quality with high microbial load may be used for preparation of an infant formula from its powdered form. As a further benefit the acidification of infant formulas has been shown to have a beneficial effect on both incidence and duration of diarrhoea, and prevention of microbial proliferation in infants during clinical studies (Chouraqui, J. P. et al. (2004) J. Pediatr. Gastroenterol. Nutr. 38: 288-292). Specifically, in a multicentre, randomised, double-blind, parallel, reference-controlled study on a population of 255 infants, fewer cases of fever and diarrhoea were observed in infants fed an acidified infant formula compared to a standard formula. Furthermore, the requirement for antibiotic treatment was lower in infants fed the acidified infant formulas. The fermented potato protein-based infant formulas of the present invention provides access to the same beneficial effects.

In addition, the inventors have found potato protein to have a well balanced amino acid profile, which is closer to that of human milk than rice or soy protein. Accordingly, less addition of free amino acids is required to provide a composition with the required nutritional profile, which renders the resulting product more cost effective and gives it a more palatable taste. As a result of their lower allergen profile, the potato protein components do not require extensive hydrolysis, which provides significant benefits in terms of cost and for the development of an infant, because the intact or slightly hydrolysed proteins facilitate improved gut maturation.

In addition, use of potato protein provides for good acceptance, for example in terms of taste and texture of the nutritional composition.

Accordingly, in one aspect the invention provides a nutritional composition obtainable by fermenting a mixture comprising protein, carbohydrate and fat, wherein the major source of protein is potato protein, and wherein the mixture is fermented by lactic acid-producing bacteria.

In a particularly preferred embodiment, the nutritional composition does not comprise dairy protein.

In a preferred embodiment, the major source of protein in the nutritional composition is potato protein and the remaining protein is plant protein. In a preferred embodiment, the major source of protein in the mixture (i.e. the mixture that is fermented) is potato protein and the remaining protein is plant protein.

The term "major source of protein is potato protein" means that the largest fraction of the total protein by weight in a composition (e.g. the mixture that is fermented and/or the final nutritional composition) originates from potato protein.

In one embodiment, at least about 50%, 55%, 60%, 65%, 70%, 75%, 80%, 85%, 90% or 95%, preferably 75%, by weight of the total protein in the nutritional composition is potato protein. In one embodiment, at least about 50%, 55%, 60%, 65%, 70%, 75%, 80%, 85%, 90% or 95%, preferably 75%, by weight of the total protein in the mixture (i.e. the mixture that is fermented) is potato protein.

In a preferred embodiment, 100% by weight of the total protein in the nutritional composition is potato protein. In another preferred embodiment, 100% by weight of the total protein in the mixture (i.e. the mixture that is fermented) is potato protein. The source of potato protein may be, for example, a high (e.g. greater than 35 kDa) or low (e.g. less than 35 kDa) molecular mass potato protein fraction, preferably a low (e.g. less than 35 kDa) molecular mass potato protein fraction.

In a preferred embodiment, the protein (in particular, the potato protein) is intact protein. Preferably, the protein has not been subjected to artificial hydrolysis.

In another embodiment, the protein (in particular, the potato protein) is partially hydrolysed protein.

In another embodiment, the protein (in particular, the potato protein) is extensively hydrolysed protein.

In one embodiment, the lactic acid-producing bacteria are lactic acid bacteria.

In one embodiment, the lactic acid-producing bacteria comprise bacteria of the genera *Streptococcus*, *Lactococcus*, *Bifidobacterium* and/or *Lactobacillus*.

In one embodiment, the lactic acid-producing bacteria comprise *Streptococcus salivarius* subsp. *thermophilus*, *Lactococcus lactis*, *Bifidobacterium longum*, *Lactobacillus acidophilus*, *Lactobacillus delbrueckii* subsp. *bulgaricus*, *Lactobacillus paracasei*, *Lactobacillus rhamnosus*, *Lactobacillus plantarum*, *Lactobacillus johnsonii*, *Lactobacillus helveticus* and/or *Bifidobacterium lactis*.

In a preferred embodiment, the lactic acid-producing bacteria comprises *Streptococcus salivarius* subsp. *thermophilus*.

In another preferred embodiment, the lactic acid-producing bacteria comprises *Lactococcus lactis*.

In one embodiment, the lactic acid-producing bacteria comprise *Streptococcus thermophilus* ST496, *Lactococcus lactis* NCC 2415 and/or *Bifidobacterium longum* BL999.

In another embodiment, the lactic acid-producing bacteria comprise *Bifidobacterium lactis* BL818, *Lactobacillus paracasei* ST11, *Lactobacillus rhamnosus* LPR and/or *Lactobacillus johnsonii* La1.

Preferably, the lactic acid-producing bacteria comprise *Streptococcus thermophilus* ST496 and/or *Lactococcus lactis* NCC 2415.

In a particularly preferred embodiment, the lactic acid-producing bacteria comprises *Streptococcus thermophilus* ST496.

In one embodiment, a single species of lactic acid-producing bacteria is used in the fermentation.

In another embodiment, a combination of 2, 3, 4, 5 or more, preferably 2, species of lactic acid-producing bacteria are used in the fermentation.

In one embodiment, a combination of *Streptococcus salivarius* subsp. *thermophilus* and *Lactobacillus delbrueckii* subsp. *bulgaricus* are used in the fermentation.

In another embodiment, a combination of *Streptococcus salivarius* subsp. *thermophilus* and *Lactobacillus acidophilus* are used in the fermentation.

In one embodiment, the nutritional composition further comprises free amino acids.

In one embodiment, the nutritional composition does not comprise a further emulsifier. The potato protein may provide sufficient function as an emulsifier.

In a preferred embodiment, the nutritional composition is an infant formula or yoghurt-like product. Preferably, the nutritional composition is an infant formula.

In a preferred embodiment, the nutritional composition (e.g. the infant formula) is for a subject (e.g. an infant) with cow's milk protein allergy.

In one embodiment, the infant formula is in the form of a powder or liquid. The liquid may be, for example, a concentrated liquid infant formula or a ready-to-feed formula. In one embodiment, the infant formula is in the form of a reconstituted infant formula (i.e. a liquid infant formula that has been reconstituted from the powdered form). Preferably, the infant formula is in the form of a powder.

The nutritional composition (e.g. the infant formula) may further comprise lactose. The mixture (i.e. the mixture that is fermented) further comprises lactose.

In one embodiment, the nutritional composition (e.g. the infant formula) further comprises probiotics. In one embodiment, the nutritional composition (e.g. the infant formula) does not comprise probiotics.

In one embodiment, the nutritional composition (e.g. the infant formula) further comprises nucleotides. In one embodiment, the nutritional composition (e.g. the infant formula) does not comprise nucleotides.

In one embodiment, the infant formula comprises:
(a) 1.8-3.2 g protein per 100 kcal;
(b) 9-14 g carbohydrate per 100 kcal; and
(c) 4.0-6.0 g lipids per 100 kcal.

In one embodiment, the nutritional composition has a pH of about 4-5.

In another aspect, the invention provides a method for producing a nutritional composition comprising the steps:
(a) providing a solution comprising protein, carbohydrate and fat, wherein the major source of protein is potato protein;
(b) adding a lactic acid-producing bacteria; and
(c) fermenting the solution of step (b).

Preferably, the nutritional composition, protein and/or lactic acid-producing bacteria are as disclosed herein. In a preferred embodiment, the nutritional composition is an infant formula disclosed herein.

In one embodiment, the fermentation of step (c) is for about 1-20, 1-15, 1-10, 2-20, 2-15, 2-10, 3-20, 3-15, 3-10, 4-20, 4-15 or 4-10 hours, preferably 4-10 hours.

In one embodiment, the fermentation of step (c) is at a temperature of about 20-45° C. or 30-45° C., preferably 30-45° C.

In one embodiment, the fermentation of step (c) is for about 4-10 hours at a temperature of about 20-45° C., preferably about 30-45° C.

In one embodiment, the fermentation of step (c) comprises stirring. In one embodiment, the mixture is not stirred during the fermentation of step (c).

In one embodiment, the fermentation of step (c) is continued until the solution reaches a pH of about 3.8-5.5. Preferably, the fermentation of step (c) is continued until the solution reaches a pH of about 4.8-5.2.

In one embodiment, the solution is adjusted to a pH of about 4.5-7.5, preferably about 5.8-5.9 at the start of the fermentation of step (c).

In another aspect, the invention provides a nutritional composition obtainable by the method of the invention.

In another aspect, the invention provides the use of lactic acid-producing bacteria for the manufacture of a fermented nutritional composition, wherein the major source of protein in the nutritional composition is potato protein.

The lactic acid-producing bacteria, nutritional composition and/or protein may be as disclosed herein.

In another aspect, the invention provides a method for feeding a subject comprising administering to the subject the nutritional composition of the invention.

In a preferred embodiment, the subject is an infant. Particularly preferably, the subject has cow's milk protein allergy.

In another aspect, the invention provides the nutritional composition of the invention for use in feeding a subject, preferably an infant, having cow's milk protein allergy.

DETAILED DESCRIPTION OF THE INVENTION

Figure 1:
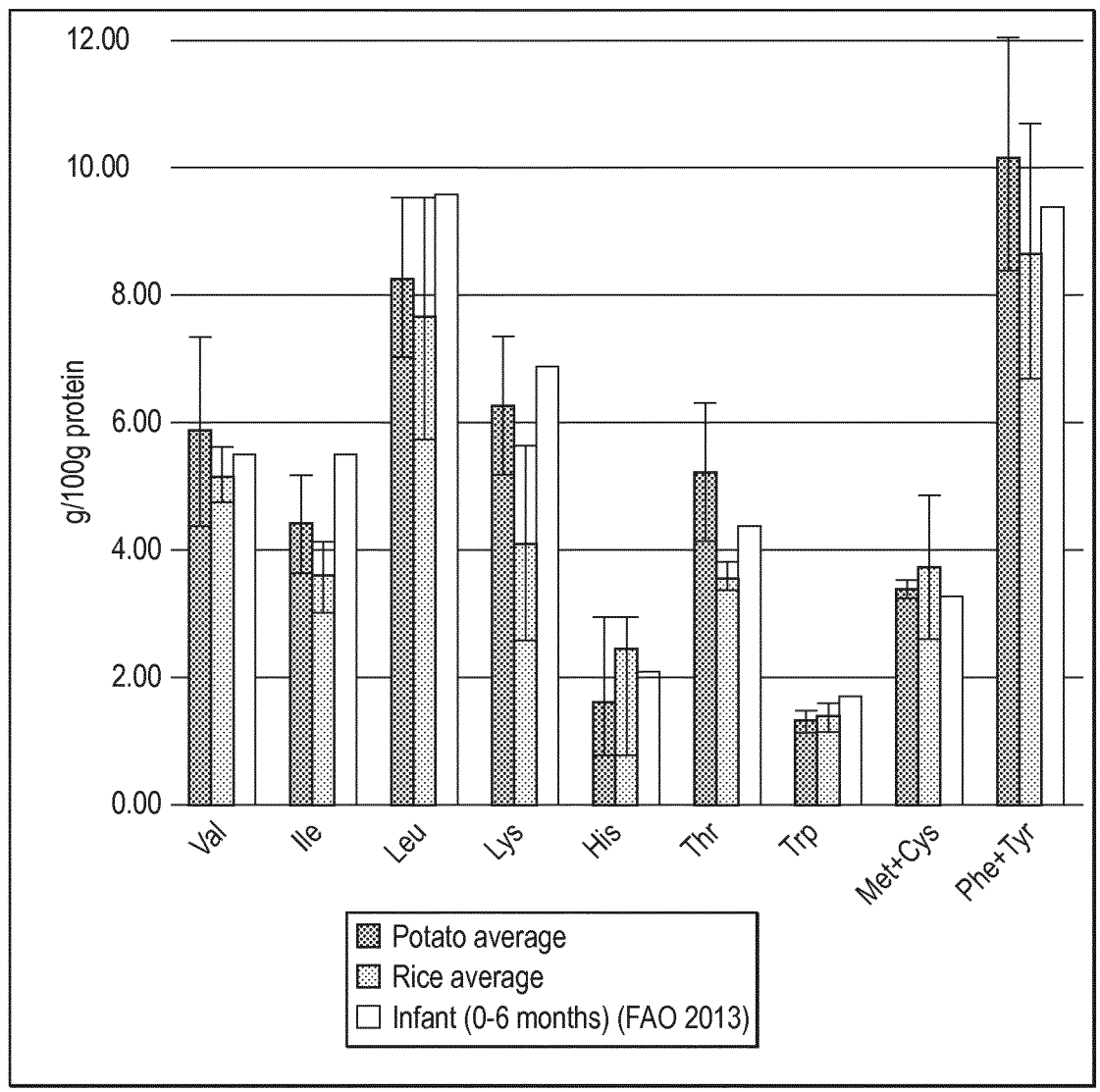
FIG. 1 Comparison of essential amino acid levels between potato and rice protein, and FAO 2013 recommendations.

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

Allergy

The term "allergy" refers to a hypersensitivity of the immune system to a substance which is normally tolerated. The allergy may be an allergy detected by a medical doctor.

The term "food allergy" refers to an allergy with respect to a nutritional composition.

Infant formulas are typically formulated with cow's milk protein. For example, bovine whey protein and/or casein are often used as the protein source in infant formulas. However, some infants exhibit an allergy to cow's milk proteins, making such formulas unsuitable.

Allergies to cows' milk and to infant formulas containing cow's milk protein may be due to the differences between the proteins in cows' milk and those in human milk. The principal recognised cow's milk allergens are alpha-lactalbumin (aLA), beta-lactoglobulin (bLG) and bovine serum albumin (BSA).

Subjects

The subjects referred to in the present disclosure as the target of the nutritional compositions disclosed herein are human subjects. Preferably, the subjects are infants.

The term "infant" refers to a child under the age of 12 months, for example a child between 0 and 6 months of age.

In another embodiment, the subjects are 12-36 months of age. The nutritional compositions of the invention that may be used for such subjects may be follow on formulas.

Nutritional Composition

The term "nutritional composition" refers to a composition that provides nutrition. The composition preferably includes protein, carbohydrate, fat and/or other components (e.g. vitamins and minerals) useful for nutrition of a subject. The levels of the individual components in a nutritional composition may be selected so as to provide tailored nutritional intake for an individual.

In a preferred embodiment, the nutritional composition is an infant formula.

In another embodiment, the nutritional composition is a yoghurt-like product, preferably a yoghurt-like product suitable for feeding infants.

In another embodiment, the nutritional composition is a follow on formula.

Infant Formula

The term "infant formula" may refer to a foodstuff intended for particular nutritional use by infants during the first year of life and satisfying by itself the nutritional requirements of this category of person, as defined in European Commission Directive 2006/141/EC of 22 Dec. 2006.

Infants can be fed solely with infant formulas or the infant formula can be used as a complement of human milk.

The term "infant formula" includes hypoallergenic infant formulas. A hypoallergenic composition is a composition which is unlikely to cause allergic reactions.

The infant formula of the invention may be in the form of a powder or liquid. The liquid may be, for example, a concentrated liquid infant formula or a ready-to-feed formula. The infant formula may be in the form of a reconstituted infant formula (i.e. a liquid infant formula that has been reconstituted from the powdered form). Preferably, the infant formula is in the form of a powder.

The powder is preferably capable of being reconstituted into a liquid composition suitable for feeding an infant, for example by the addition of water. Similarly, the concentrated liquid infant formula is preferably capable of being diluted into a liquid composition suitable for feeding an infant, for example by the addition of water.

In one embodiment, the infant formula has an energy density of about 60-70 kcal per 100 mL, when formulated as instructed.

Protein

The term "protein" refers to polymers of amino acids, and includes polypeptides and peptides. The term "protein" does not encompass free amino acids, which may also be present in the nutritional composition (e.g. infant formula) of the invention.

The protein content of the infant formula of the invention is preferably in the range 1.8-3.2 g protein per 100 kcal. In a preferred embodiment, the protein content of the infant formula of the invention is in the range 1.8-2.8 g protein per 100 kcal. The nutritional compositions of the invention comprises potato protein as the major protein source.

In one embodiment, at least about 50%, 55%, 60%, 65%, 70%, 75%, 80%, 85%, 90% or 95%, preferably at least about 75%, more preferably 100%, by weight of the total protein in the nutritional composition is potato protein. In one embodiment, at least about 50%, 55%, 60%, 65%, 70%, 75%, 80%, 85%, 90% or 95%, preferably at least about 75%, more preferably 100%, by weight of the total protein in the mixture (i.e. the mixture that is fermented) is potato protein.

The remaining protein in the nutritional composition of the invention may be any protein which is suitable for use in a nutritional composition, in particular an infant formula.

In a particularly preferred embodiment, the nutritional composition does not comprise dairy protein. Accordingly, in a preferred embodiment 100% by weight of the total protein is non-dairy protein.

In a preferred embodiment, 100% by weight of the total protein is plant protein.

Example plant proteins that may optionally be used in the infant formula of the invention, in addition to the potato protein, include, pea, rice, quinoa, oat, sunflower or coconut proteins, or combinations thereof.

Further example non-dairy proteins for use in the infant formula of the invention include algal protein or leaf protein.

In a preferred embodiment, the major source of protein in the nutritional composition is potato protein and the remaining protein is plant protein. In a preferred embodiment, the major source of protein in the mixture (i.e. the mixture that is fermented) is potato protein and the remaining protein is plant protein.

In a preferred embodiment, 100% by weight of the total protein in the nutritional composition is potato protein. In another preferred embodiment, 100% by weight of the total protein in the mixture (i.e. the mixture that is fermented) is potato protein.

Potato protein for use in the nutritional compositions of the invention is readily accessible or available, for example as concentrates or isolates, for example from commercial sources.

Potato protein may be extracted from potato tuber juice, which may itself be separated from potato solids by any of a number of suitable techniques known in the art. Chromatographic techniques may be used to purify potato proteins from the tuber juice in a similar manner to the isolation of milk proteins. Once isolated, the potato protein may be concentrated and subjected to temperature treatment and/or pH adjustment. Further steps may include, for example, removal of triglycoalkaloids, spray drying and/or UV treatment.

Suitable potato protein sources include complete potato protein extract (i.e. extract not subjected to fractionation by molecular mass); and potato protein fractionated by molecular mass, for example a high molecular mass fraction (e.g. greater than 35 kDa); or a low molecular mass fraction (e.g. less than 35 kDa). In one embodiment, the potato protein source is a low molecular mass potato protein fraction of less than 35 kDa.

The protein may be, for example, intact protein or hydrolysed protein (e.g. partially hydrolysed protein). Preferably, the protein is intact protein.

Hydrolysis of protein may in general be termed "partial" or "extensive" depending on the degree to which hydrolysis is carried out. Protein hydrolysates may have an extent of hydrolysis that is characterised by NPN/TN %, which refers to the non-protein nitrogen divided by the total nitrogen× 100. The non-protein nitrogen refers to amino nitrogen that is free to react with a reagent such as trinitrobenzenesulfonic acid (TNBS). NPN/TN % may be measured as described in Adler-Nissen (Adler-Nissen, J. (1979) J. Agric. Food Chem. 27: 1256-1262).

The term "extensive hydrolysis" may refer to hydrolysis that provides protein that has a NPN/TN % greater than 95%. The term "partial hydrolysis" may refer to hydrolysis that provides protein that has a NPN/TN % in the range 70-85%.

In one embodiment, the protein has an NPN/TN % between 25-90%, 70-90% or 70-85%, preferably between 70-85%. In another embodiment, the protein has an NPN/TN % between 25-55%, 25-50% or 50-55%.

In one embodiment, 60-70% of the protein population has a molecular mass of less than 5000 Da.

In another embodiment, the protein has an NPN/TN % greater than 95%. These are "extensive" hydrolysates.

In one embodiment, 60-70% of the protein population has a molecular mass of less than 3000 Da. In one embodiment, at least 95% of the protein population has a molecular mass of less than 3000 Da.

Proteins for use in the nutritional composition of the invention may be hydrolysed by any suitable method known in the art. For example, proteins may enzymatically hydrolysed, for example using a protease.

For example, protein may be hydrolysed using alcalase (e.g. at an enzyme:substrate ratio of about 2-15% by weight and for a duration of about 1-5 hours).

Free Amino Acids

The nutritional compositions and mixtures (i.e. the mixture that is fermented) disclosed herein may further comprise free amino acids. Such free amino acids provide a protein equivalent source.

Free amino acids may be incorporated in the nutritional compositions and mixtures (i.e. the mixture that is fermented) disclosed herein to supplement the amino acids comprised in the protein. The levels of free amino acids may be chosen to provide an amino acid profile that is sufficient for nutrition of a specific subject, in particular an amino acid profile that satisfies nutritional regulations (e.g. European Commission Directive 2006/141/EC). Preferably, the levels of free amino acids are chosen to provide sufficient infant nutrition.

Example free amino acids for use in the nutritional compositions and mixtures (i.e. the mixture that is fermented) disclosed herein include histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof.

Carbohydrate

The carbohydrate content of the infant formula of the invention is preferably in the range 9-14 g carbohydrate per 100 kcal.

The carbohydrate may be any carbohydrate which is suitable for use in a nutritional composition, in particular an infant formula.

Example carbohydrates for use in the nutritional compositions and mixtures (i.e. the mixture that is fermented) disclosed herein include lactose, saccharose, maltodextrin and starch. Mixtures of carbohydrates may be used.

In one embodiment, at least 40%, 50%, 60% of 70%, 80%, 90% or 95% by weight of the total carbohydrate in the nutritional composition is lactose. In another embodiment, 100% by weight of the total carbohydrate in the nutritional composition is lactose. The mixture (i.e. the mixture that is fermented) further comprises lactose. In one embodiment, at least 40%, 50%, 60%, 70%, 80%, 90% or 95% by weight of the total carbohydrate in the mixture (i.e. the mixture that is fermented) is lactose. In another embodiment, 100% by weight of the total carbohydrate in the mixture (i.e. the mixture that is fermented) is lactose.

In one embodiment, the carbohydrate comprises lactose and maltodextrin.

In one embodiment, the carbohydrate comprises maltodextrin.

Fat

The fat content of the infant formula of the invention is preferably in the range 4.0-6.0 g lipids per 100 kcal.

The fat may be any lipid or fat which is suitable for use in a nutritional composition, in particular an infant formula.

Example fats for use in the nutritional compositions and mixtures (i.e. the mixture that is fermented) disclosed herein include sunflower oil, low erucic acid rapeseed oil, safflower oil, canola oil, olive oil, coconut oil, palm kernel oil, soybean oil, fish oil, palm oleic, high oleic sunflower oil and high oleic safflower oil, and microbial fermentation oil containing long chain, polyunsaturated fatty acids.

The fat may also be in the form of fractions derived from these oils, such as palm olein, medium chain triglycerides and esters of fatty acids such as arachidonic acid, linoleic acid, palmitic acid, stearic acid, docosahexaenoic acid, linolenic acid, oleic acid, lauric acid, capric acid, caprylic acid, caproic acid, and the like.

Further example fats include structured lipids (i.e. lipids that are modified chemically or enzymatically in order to change their structure). Preferably, the structured lipids are sn2 structured lipids, for example comprising triglycerides having an elevated level of palmitic acid at the sn2 position of the triglyceride.

Oils containing high quantities of preformed arachidonic acid and/or docosahexaenoic acid, such as fish oils or microbial oils, may also be added.

Long chain polyunsaturated fatty acids, such as dihomo-γ-linolenic acid, arachidonic acid, eicosapentaenoic acid and docosahexaenoic acid, may be added. Willemsen et al. showed that the addition of such fatty acids supported epithelial barrier integrity and reduced IL-4 mediated permeability (Willemsen, L. E. et al. (2008) Eur. J. Nutr. 47 (4): 183-191).

Structured lipids may be added or may be omitted. Medium chain triglycerides may be added or may be omitted.

Further Ingredients

The nutritional composition of the invention preferably also contains some or all vitamins and minerals understood to be essential in the daily diet in nutritionally significant amounts. Minimum requirements have been established for certain vitamins and minerals.

Example vitamins, minerals and other nutrients for use in the nutritional composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine and L-carnitine.

Minerals are usually added in their salt form.

The nutritional composition of the invention may also comprise at least one probiotic. The term "probiotic" refers to microbial cell preparations or components of microbial cells with beneficial effects on the health or well-being of the host (Salminen, S. et al. (1999) Trends Food Sci. Technol. 10: 107-10).

In particular, probiotics may improve gut barrier function (Rao, R. K. (2013) Curr. Nutr. Food Sci. 9: 99-107).

Preferred probiotics are those which as a whole are safe and have acceptable shelf-life for products that are required to remain stable and effective for up to 24 months.

Examples of probiotic micro-organisms for use in the nutritional composition of the invention include yeasts, such as *Saccharomyces, Debaromyces, Candida, Pichia* and *Torulopsis*; and bacteria, such as the genera *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*.

Specific examples of suitable probiotic microorganisms are: *Saccharomyces cerevisiae, Bacillus coagulans, Bacillus licheniformis, Bacillus subtilis, Bifidobacterium animalis* subsp. *lactis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei, Lactobacillus curvatus, Lactobacillus delbruckii* subsp. *lactis, Lactobacillus farciminis, Lactobacillus gasseri, Lactobacillus helveticus, Lactobacillus johnsonii, Lactobacillus paracasei, Lactobacillus rhamnosus, Lactobacillus sakei, Lactococcus lactis, Micrococcus varians, Pediococcus acidilactici, Pediococcus pentosaceus, Pediococcus halophilus, Streptococcus faecalis, Streptococcus thermophilus, Staphylococcus carnosus* and *Staphylococcus xylosus*.

Preferred probiotic bacterial strains include *Lactobacillus rhamnosus* LPR (CGMCC 1.3724); *Bifidobacterium animalis* subsp. *lactis* BL818 (CNCM I-3446); and *Bifidobacterium longum* BL999 (ATCC BAA-999).

The nutritional composition of the invention may also contain other substances which may have a beneficial effect such as human milk oligosaccharides, prebiotics, lactoferrin, fibres, nucleotides, nucleosides and the like.

Lactic Acid-Producing Bacteria

The term "lactic acid-producing bacteria" refers to bacteria that are capable of producing lactic acid during fermentation.

The term "lactic acid bacteria" refers to bacteria that are in the order Lactobacillales. This includes the genera *Lactobacillus, Leuconostoc, Pediococcus, Lactococcus* and *Streptococcus*, as well as *Carnobacterium, Enterococcus, Oenococcus, Tetragenococcus, Vagococcus* and *Weisella*. Lactic acid bacteria are also capable of producing lactic acid. *Bifidobacterium* is not usually referred to as a lactic acid bacteria, because of genetic differences. However, the habitat of *Bifidobacterium* overlaps with lactic acid bacteria and it produces lactic acid as a product of fermentation.

Bacteria that produce L-(+) lactic acid are preferable over those producing D-(−) lactic acid for the fermentation.

Method for Manufacture

The nutritional composition of the invention may be prepared in any suitable manner. For example, a method for producing the nutritional composition may comprise the steps:
(a) providing a solution comprising protein, carbohydrate and fat, wherein the major source of protein is potato protein;
(b) adding a lactic acid-producing bacteria; and
(c) fermenting the solution of step (b).

In an alternative embodiment, the fat may be added after the fermentation step. For example a method for producing the nutritional composition may comprise the steps:
(a) providing a solution comprising protein and carbohydrate, wherein the major source of protein is potato protein;
(b) adding a lactic acid-producing bacteria;
(c) fermenting the solution of step (b); and
(d) adding a fat to the fermented composition of step (c).

Preferably, the nutritional composition, protein and/or lactic acid-producing bacteria are as disclosed herein. In a preferred embodiment, the nutritional composition is an infant formula disclosed herein.

In one embodiment, the fermentation of step (c) is for about 1-20, 1-15, 1-10, 2-20, 2-15, 2-10, 3-20, 3-15, 3-10, 4-20, 4-15 or 4-10 hours, preferably 4-10 hours.

In one embodiment, the fermentation of step (c) is at a temperature of about 20-45° C. or 30-45° C., preferably 30-45° C.

In one embodiment, the fermentation of step (c) is for about 4-10 hours at a temperature of about 20-45° C., preferably about 30-45° C.

In a preferred embodiment, the fermentation of step (c) is for about 4-10 hours at a temperature of about 30-45° C.

In one embodiment, the fermentation of step (c) comprises stirring. In one embodiment, the mixture is not stirred during the fermentation of step (c).

In one embodiment, the fermentation of step (c) is continued until the solution reaches a pH of about 3.8-5.5. Preferably, the fermentation of step (c) is continued until the solution reaches a pH of about 4.9-5.2.

In one embodiment, the solution of step (a) is pasteurised before addition of the lactic acid-producing bacteria.

In one embodiment, the product of step (c) is pasteurised after the fermentation.

EXAMPLES

Example 1—Nutritional Comparison Between Potato Protein and Rice Protein

Potato protein contains higher levels of the following essential amino acids compared to rice protein (FIG. 1): valine; isoleucine; leucine; lysine; threonine and aromatic amino acids.

The concentrations of tryptophan and the sulfur-containing amino acids are similar between potato and rice proteins.

However, rice protein contains higher concentrations of histidine than potato protein.

Overall, the essential amino acid concentrations in potato protein are better than rice protein, and may require lower levels of additional amino acid fortification.

Potato protein contains more essential amino acids in compliance with the FAO 2013 recommendations compared to rice protein (Table 1).

TABLE 1

Amino acid concentrations in potato and rice proteins that are complaint with the FAO 2013 recommendations for 0-6 month-old infants.

| Amino acid | Potato | Rice |
|---|---|---|
| Val | ✓ | x |
| Ile | x | x |
| Leu | x | x |
| Lys | x | x |

TABLE 1-continued

Amino acid concentrations in potato and rice proteins that are complaint with the FAO 2013 recommendations for 0-6 month-old infants.

| Amino acid | Potato | Rice |
|---|---|---|
| His | x | ✓ |
| Thr | ✓ | x |
| Trp | x | x |
| Met + Cys | ✓ | ✓ |
| Phe + Tyr | ✓ | x |

Although the levels of histidine are lower in potato protein than rice protein, and are lower than the FAO 2013 recommendations for 0-6 month-old infants, potato protein will still deliver histidine levels that are compliant with the 214 mg/d histidine suggested by Institute of Medicine of the National Academies Adequate Intake (AI) for 0-6 month-old infants.

Furthermore, although the concentrations of isoleucine, leucine, lysine and tryptophan are lower in potato compared to the FAO 2013 recommendations, these levels are similar or higher than the levels in rice. Additionally, potato protein will meet the Institute of Medicine of the National Academies AI recommendations for these amino acids, while rice protein will not meet the recommendations for isoleucine and lysine.

The concentrations for isoleucine, leucine and lysine taken from the supplier data indicates that the levels of these amino acids will be compliant with WHO 2007, 2013 and EC Directive 2006/141/EC, and codex standard (CODEX STAN 72-1981), in addition to Institute of Medicine of the National Academies AI recommendations.

Branched-Chain Amino Acids (BCAA)

Branched-chain amino acids (BCAA; leucine, isoleucine and valine) have an important role in protein synthesis. Leucine is an activator of mTOR, and promotes protein synthesis and suppress protein catabolism, resulting in maintenance of muscle protein during restricted dietary intake. Children with food allergies follow dietary restrictions, therefore they are at risk of developing malnutrition, hence consumption of plant protein with high levels of BCAAs may help maintain muscle proteins.

Additionally, the best food sources of BCAAs are meat, fish, dairy products and eggs, which may not be consumed at all, or at least consumed in smaller amounts by infants and small children with food allergies. The sum of BCAA in potato is closer to that in milk and therefore provides an advantage to children with cow's milk protein allergy. Accordingly, providing a protein source with higher levels of BCAAs may benefit this paediatric population.

Lysine and Threonine

Lysine and threonine are the first and second most limiting amino acids, respectively, for protein synthesis in human subjects consuming a predominantly cereal-based diet such as wheat and rice. The main roles of lysine and threonine are in protein synthesis. Unlike other plant proteins sources such as rice and wheat proteins, potato protein has higher levels of these two amino acids, with lysine levels close to the requirement set by the FAO 2013 recommendations and threonine levels exceeding it.

The best food sources of threonine and lysine are soy, dairy products, nuts, and fish, beef or chicken. These food sources may not be consumed at all, or at least consumed in smaller amounts by infants and small children with food allergies. Therefore providing a non-animal source of protein with high concentrations of these two amino acids will benefit this paediatric population.

Aromatic Amino Acids

Phenylalanine is a precursor for tyrosine, the neurotransmitters dopamine, norepinephrine, and adrenaline, and the skin pigment melanin. Potato protein exceeds the requirements set by the FAO 2013 recommendations for 0-6 month-old infants, while rice does not meet the recommended level.

The best food sources of phenylalanine are eggs, chicken, liver, beef, milk and soybeans. These food sources may not be consumed at all, or at least consumed in smaller amounts by infants and small children with food allergies. However, the combined levels of phenylalanine and tyrosine in potato protein are similar to those in milk, which provides an advantage to infants and children with cow's milk protein allergy.

Example 2—Fermentation of Infant Formula with Potato Protein

Material and Methods

Lab Trial 1

The infant formula bases for two variants (reference and high (greater than 35 kDa) molecular mass potato protein fraction) were prepared by mixing the relevant protein with carbohydrate (lactose and maltodextrin) and fat sources, and with minerals.

A heat treatment of 72° C. for 15 seconds in a water bath was applied.

Skim milk (commercially available liquid skim milk) was used as the source of protein in the reference recipe.

The starter culture used was Streptococcus thermophilus ST496 (CNCM I-3915).

Fermentation was carried out in duplicate for both variants in 250 mL glass bottles placed in a water bath and monitored by a CINAC system (continuous measurement of pH and acidification rate). For one bottle of each variant the fermentation was stopped after 4 h. In the remaining two bottles, the fermentation was continued for an additional hour with the aim to reach a lower pH.

Lab Trial 2

In the second trial, only the potato protein base was tested. In this trial, the base was prepared on a larger scale (pilot plant) and then fermented again in the lab. Otherwise, base preparation and fermentation was similar to that carried out in Lab trial 1.

Lab Trial 3

In the third lab trial, a different potato protein (low (less than 35 kDa) molecular mass fraction) was tested, which has better solubility at low pH. Additionally, different strains (Table 1) were tested for the fermentation.

The target inoculation rate was increased to $1.0 \times 10^8$ cfu/g in order to achieve a faster acidification without having to carry out a starter fermentation beforehand. Fermentation temperatures were chosen between 30-40° C. depending on the optimum temperatures for the different strains. Otherwise, base preparation and fermentation was similar to that carried out in Lab trial 1.

TABLE 2

Strains used for fermentation in lab trial 3.

| Strain abbreviation | Species | Culture collection number |
|---|---|---|
| LPR | Lactobacillus rhamnosus | CGMCC 1.3724 |
| ST11 | Lactobacillus paracasei | CNCM I-2116 |
| BL818 | Bifidobacterium animalis subsp. lactis | CNCM I-3446 |
| BL999 | Bifidobacterium longum | ATCC BAA-999 |
| La1 | Lactobacillus johnsonii | CNCM I-1225 |
| ST496 | Streptococcus thermophilus | CNCM I-3915 |
| NCC 2415 | Lactococcus lactis | CNCM I-1962 |

Analysis

Cell count analysis was performed by classical plating methods for all trials (summarised in James Monroe Jay, Martin J. Loessner, David A. Golden. 2005. Modern food microbiology. 7th edition, Springer Science, New York, N.Y.).

Results and Discussion

Lab Trial 1

Before Fermentation

The base mixes before fermentation differed in appearance. The reference was a milky liquid, somewhat translucent, with an oil layer on the top (no homogenisation was done) and it foamed after shaking. The variant with the high molecular mass potato protein fraction was more viscous, grey-beige in colour and not translucent. The oil did not separate in this variant and no foam formed after shaking.

The pH of the base mixes before heat treatment was 6.51 at 34.7° C. for the reference and 6.08 at 34.8° C. for the potato protein variant.

Fermentation

Figure 2:
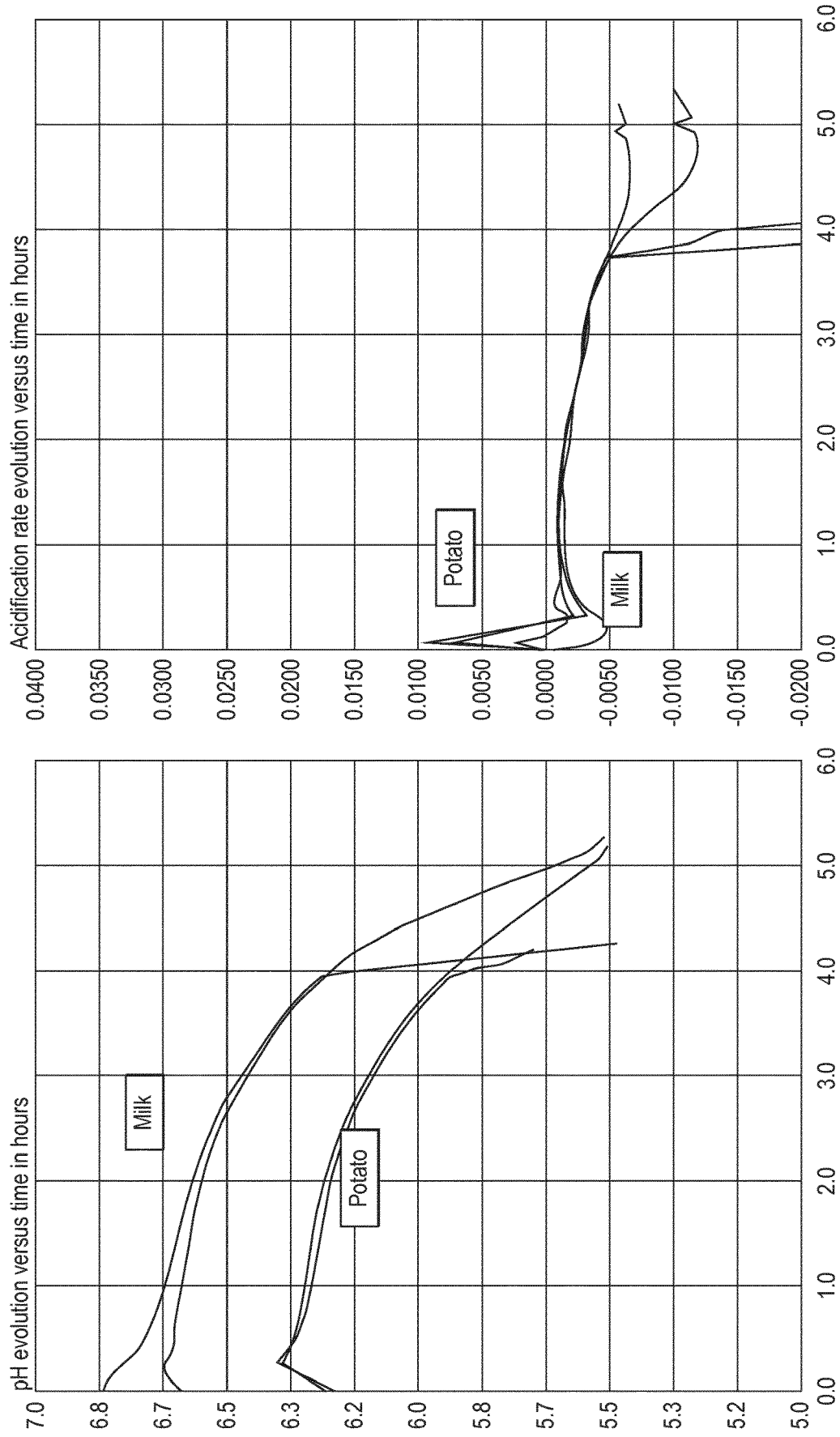
FIG. 2 Fermentation profiles of two variants (a milk based reference experiment and an experiment using potato protein, both fermented using *Streptococcus thermophilus* ST496) in duplicate. One of each variant was stopped after 4 h.

FIG. 2 shows the fermentation profiles (pH change and acidification rate over time) of both variants in duplicate.

The starting pH differed for the two different variants, but the acidification rates were very similar.

Figure 3:
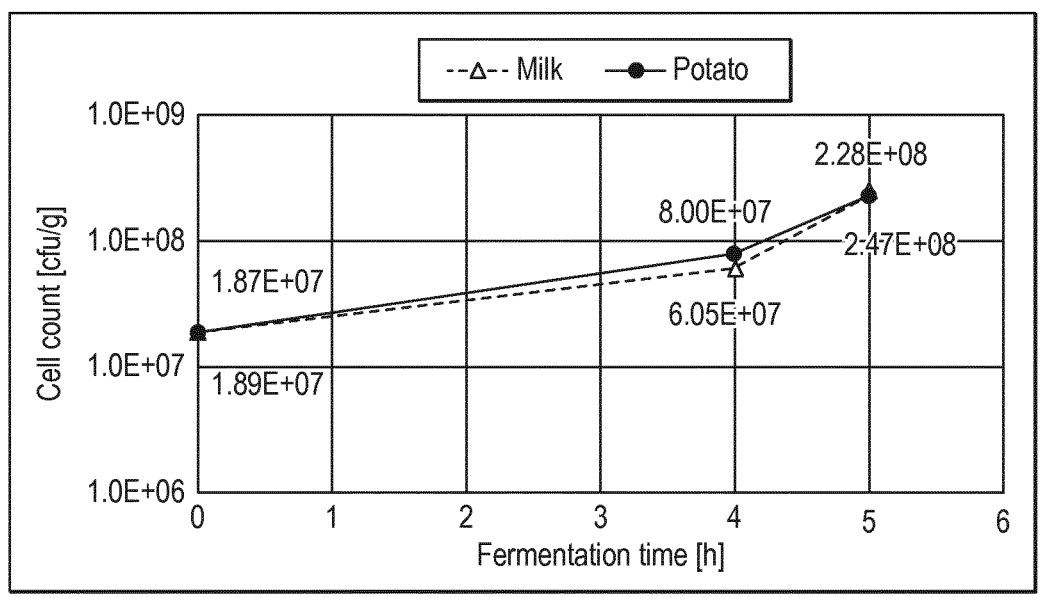
FIG. 3 Cell counts of *S. thermophilus* at different time points during the fermentation for two variants (a milk based reference experiment and an experiment using potato protein).

Cell count analysis (FIG. 3) showed the expected starting cell count (theoretically $1.0\text{-}2.0\times10^7$ cfu/g) and comparable growth in both variants.

Overall, the fermentation performance of the milk based reference and the potato based variant was very similar.

Sample Evaluation After Fermentation

The fermentation with S. thermophilus ST496 in both variants led to a production of lactic acid from the lactose present (decreasing pH during fermentation). In the milk based variant, the lactic acid induced coagulation of the milk proteins and a typical yoghurt texture was formed. However, in the potato-based variant it appeared that the proteins and the texture remained largely unchanged.

It was not clear if S. thermophilus ST496 would be able to grow in a potato protein base. Since the strain grew just as well in the potato protein-based medium as in the milk-based medium and no other nitrogen source was added, it appears that S. thermophilus ST496 is able to use the potato protein as a nitrogen source for growth.

Lab Trial 2

Before Fermentation

The potato protein (high molecular mass fraction) base was prepared in the pilot plant. Appearance was similar to lab trial 1.

Fermentation

Figure 5:
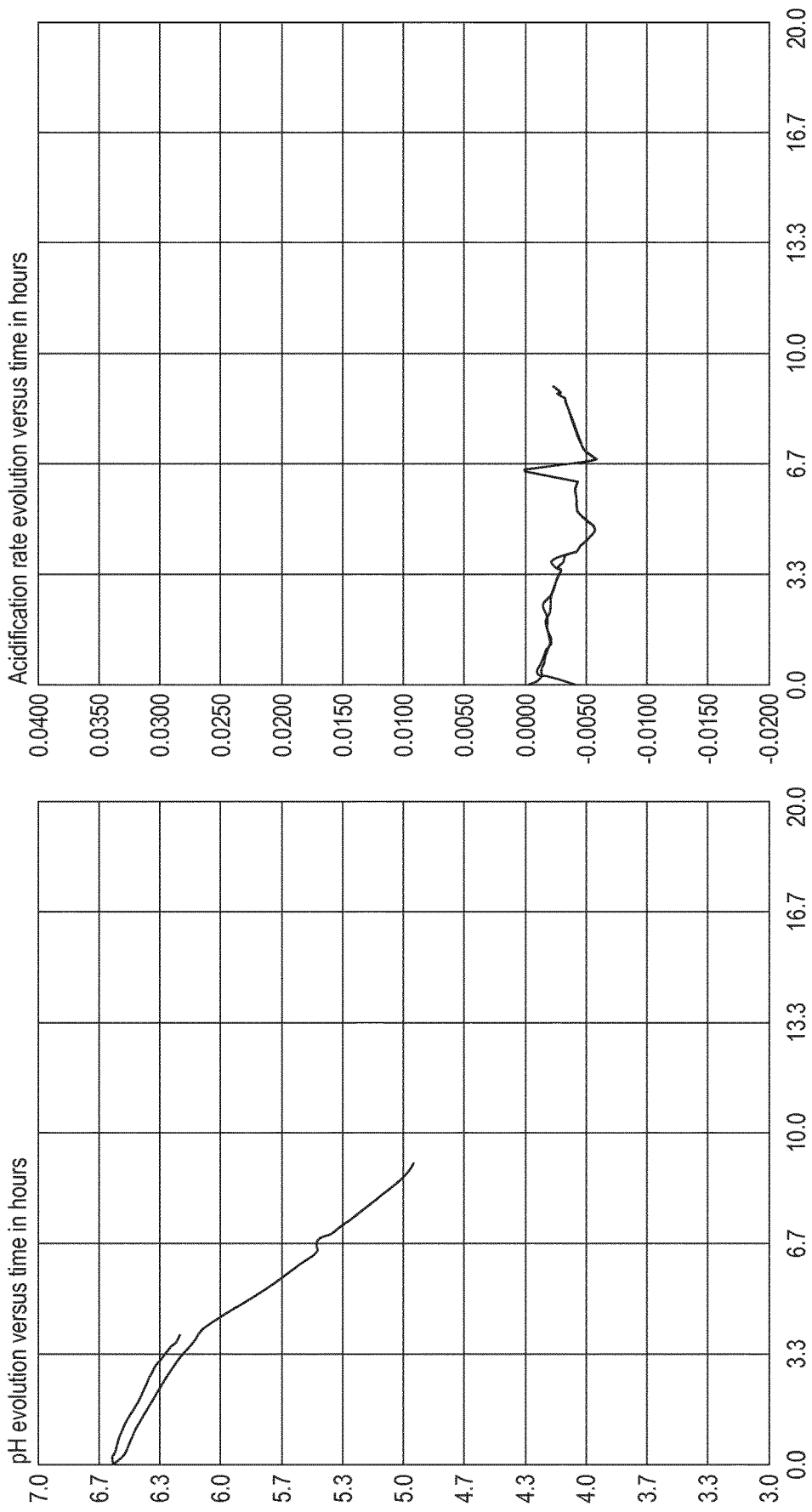
FIG. 5 Fermentation profiles of an experiment using potato protein in duplicate. One fermentation was stopped after 4 h, another was stopped when pH 4.95 was reached.

FIG. 5 shows the fermentation profile of the potato protein base. The fermentation proceeded at a similar rate as in the first lab test, reaching pH 5.7 after about 5 h fermentation. One fermentation was stopped after 4 h, while the second was continued until pH 4.95 was reached.

Figure 4:
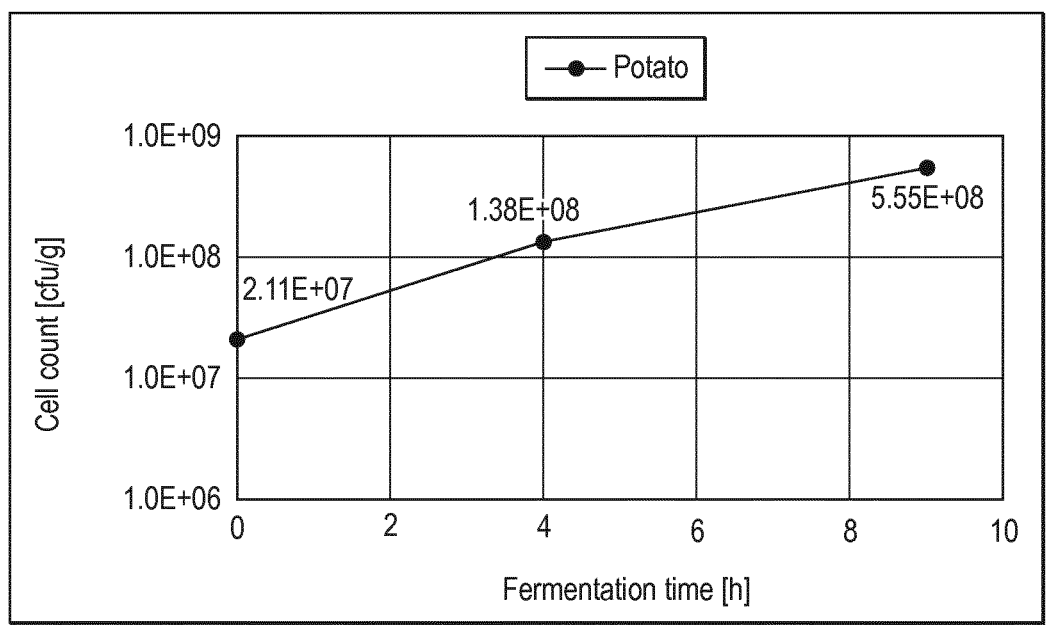
FIG. 4 Cell counts of *S. thermophilus* at different time points during the fermentation using potato protein.

FIG. 4 displays the cell counts of S. thermophilus during the fermentation.

Sample Evaluation After Fermentation

The samples were evaluated after fermentation (Table 2).

TABLE 3

Lab trial 2 - Sensory evaluation.

| What | Visual | Smell/Taste |
|---|---|---|
| Potato (high molecular mass fraction) 4 hours fermentation non-pasteurised | greyish colour | strong potato taste, not sweet powdery/sandy mouthfeel |
| Potato (high molecular mass fraction) 9 hours fermentation non-pasteurised | whiter colour grey/white | yoghurt-like smell yoghurt taste with powdery/sandy mouthfeel |

After 2 days storage in the fridge, the samples fermented for 4 h (pasteurised and non-pasteurised) were somewhat lumpy, while the sample fermented for 9 h remained smooth with a clear yoghurt smell.

Lab Trial 3

Before Fermentation

Due to the different potato protein used in this trial (low molecular mass fraction), the base was more acidic with a pH of 5.1 before fermentation. In order to have some room for fermentation to take place, the pH of the base was increased to about pH 5.8-5.9 with NaOH. The base was much less viscous and whiter than in the previous 2 trials, which may be due to the use of the low rather than high molecular mass potato protein fraction. As no homogenisation was carried out and the viscosity was low, an oil layer formed on the top with a foam layer above.

Fermentation

In all samples, the oil and foam layer remained on the top of the base during the fermentation.

Figure 6:
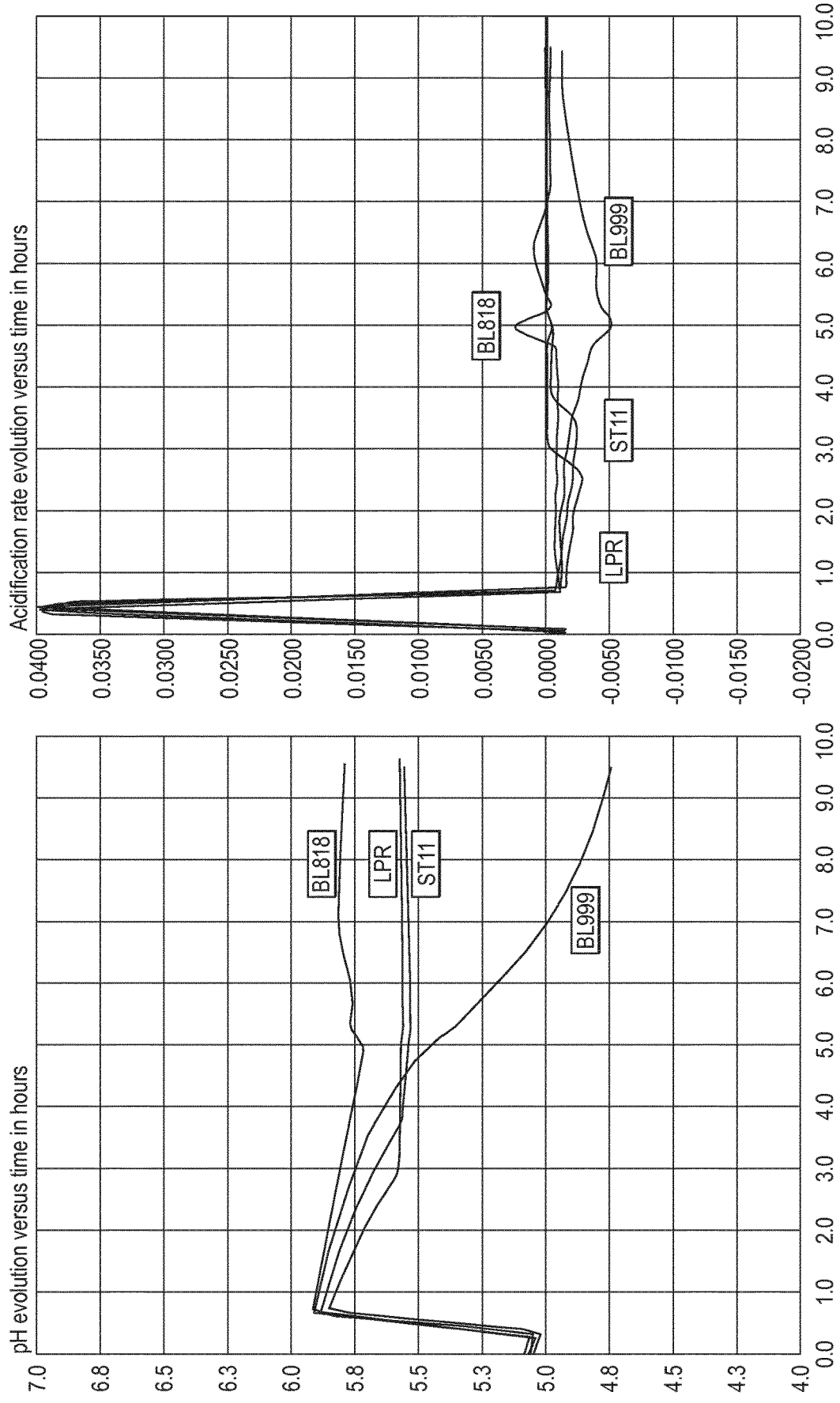
FIG. 6 Fermentation profiles of the low (less than 35 kDa) molecular mass potato protein fraction base fermented with four different strains (*L. rhamnosus* LPR, *B. lactis* BL818, *B. longum* BL999 and *L. paracasei* ST11).
Figure 7:
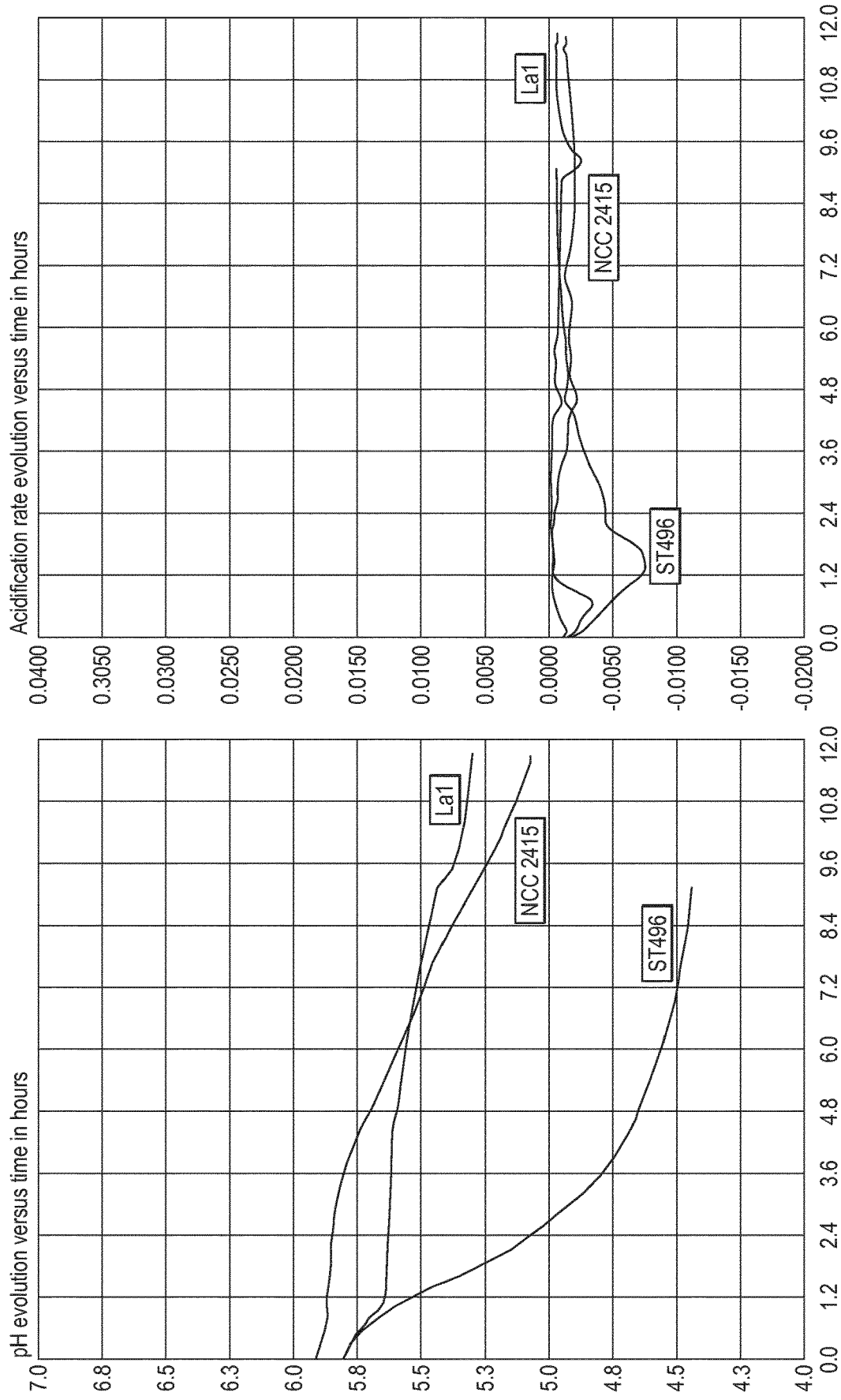
FIG. 7 Fermentation profiles of the low (less than 35 kDa) molecular mass potato protein fraction base fermented with three different strains (*S. thermophilus* ST496, *L. johnsonii* La1 and *L. lactis* NCC 2415).

FIG. 6 and FIG. 7 show the fermentation profiles of the samples fermented with *L. rhamnosus* LPR, *B. lactis* BL818, *B. longum* BL999 and *L. paracasei* ST11, and with *S. thermophilus* ST496, *L. johnsonii* La1 and *L. lactis* NCC 2415. In all cases only one of the duplicates is shown in the graphs—the other duplicates were stopped after about 4.5 h fermentation time for cell count analysis. The pH increase at the beginning in FIG. 6 was due to the pH adjustment that was carried out after it was found that the pH was already quite low with this potato protein. For the experiment shown in FIG. 7 the pH adjustment was done before inoculation. Depending on the types of mineral salts used in the nutritional composition this pH adjustment may or may not be required.

Figure 8:
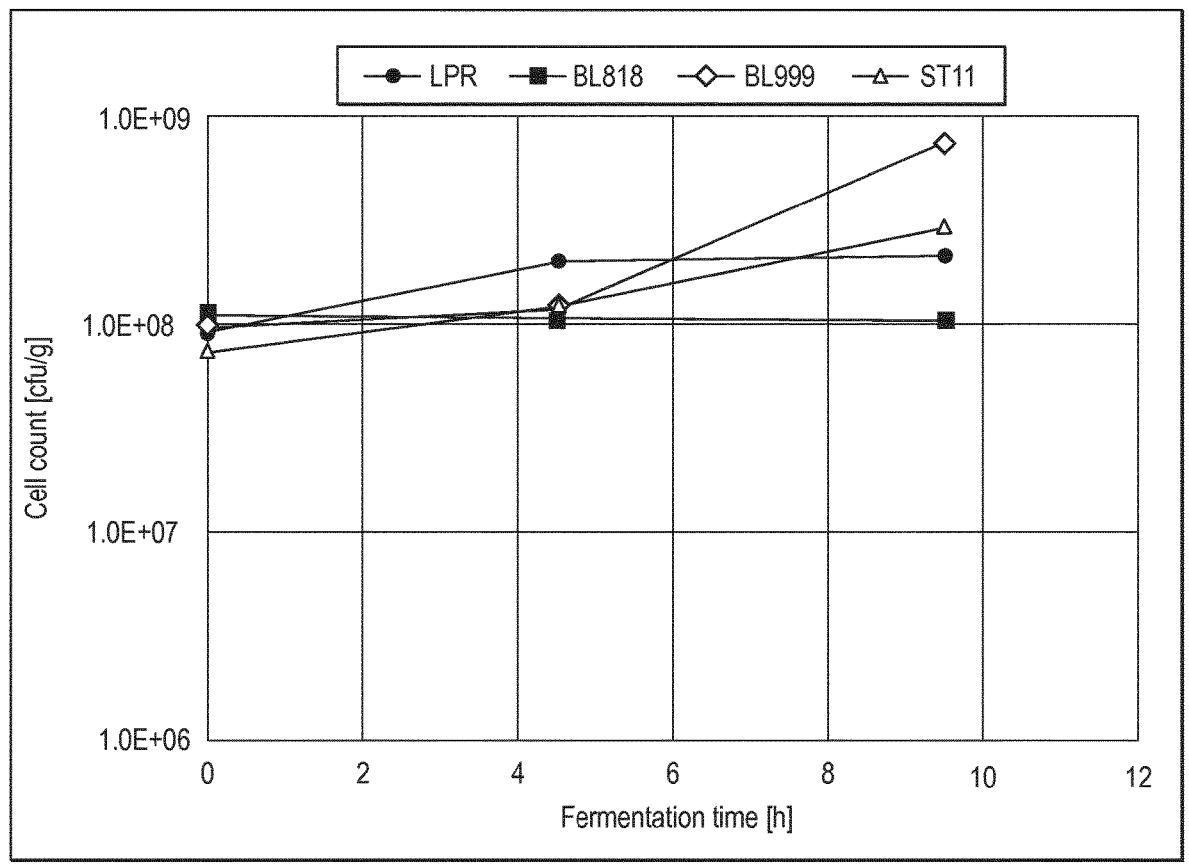
FIG. 8 Cell counts of four different strains (*L. rhamnosus* LPR, *B. lactis* BL818, *B. longum* BL999 and *L. paracasei* ST11) at different time points during the fermentation.

With *L. rhamnosus* LPR and *L. paracasei* ST11, the fermentation proceeded initially quite well, but stopped after about 3-4 hours. This was probably because both strains are not able to grow on lactose (although many strains of these species are able to use lactose), but were using limited amounts of other sugars available from the maltodextrin. Both strains showed some growth (see FIG. 8 for cell counts). BL999 grew well and acidified to pH 4.8 within 9.5 h.

*S. thermophilus* ST496 confirmed again that it grows and acidifies well in this formula. Due to the higher inoculation rate in this trial compared to the previous trials, acidification was faster—pH 4.8 was reached in less than 4 h. The fermentation was continued until about 9 h fermentation time, at which point the pH was 4.44, however, no growth seems to have occurred in this last part of the fermentation—probably due to the low pH.

Figure 9:
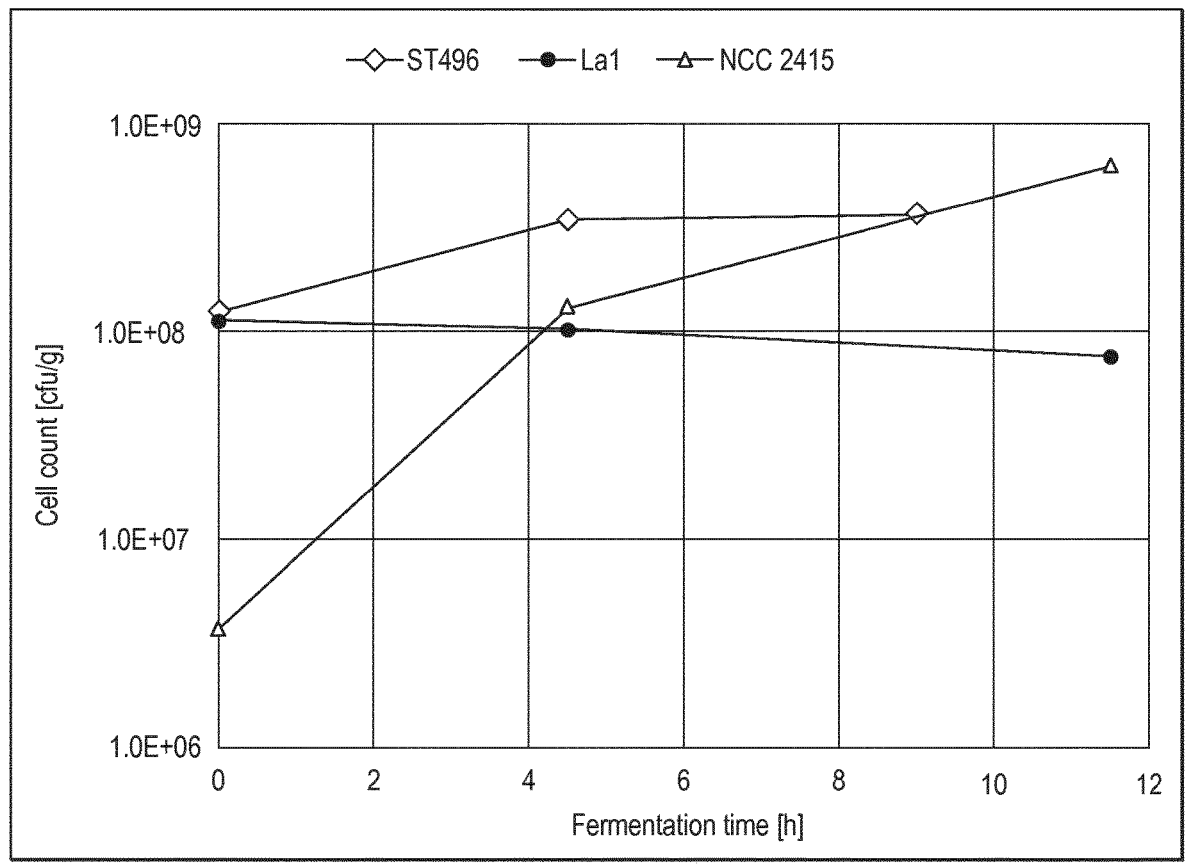
FIG. 9 Cell counts of three different strains (*S. thermophilus* ST496, *L. johnsonii* La1 and *L. lactis* NCC 2415) at different time points during the fermentation.

For *L. lactis* the inoculation was much lower than for the other strains (FIG. 9), due to the use of a non-concentrated glycerol stock instead of a frozen concentrate. Still the culture reached pH 5.08 after 11.5 h fermentation time and caught up in terms of cell counts through fast growth.

Table 4 summarises the findings on acidification performance and growth of all strains. In this sense, the best strains are *B. longum* BL999, *S. thermophilus* ST496 and *L. lactis* (NCC 2415).

TABLE 4

Lab trial 3 - Summary of fermentation performance and growth of the various strains in potato-based formula (low molecular mass potato protein fraction).

| Strain | Acidification | Growth |
|---|---|---|
| *L. rhamnosus* LPR | + | + |
| *L. paracasei* ST11 | + | + |
| *B. lactis* BL818 | 0 | 0 |
| *B. longum* BL999 | ++ (use of lactose) | ++ |
| *L. johnsonii* La1 | + | 0 |
| *S. thermophilus* ST496 | +++ (use of lactose) | ++ |
| *Lactococcus lactis* NCC 2415 | ++ (use of lactose) | +++ |

0 = none, + = some, ++ = good, +++ = very good.

Sample Evaluation After Fermentation

The samples were evaluated after fermentation. The samples appeared visually unchanged after fermentation and were still liquid. For the tasting a choice was made of the most promising samples (end of fermentation with *B. longum* BL999, *S. thermophilus* ST496 and *L. lactis* NC 2415) and one sample without fermentation of lactose as a negative control (*L. paracasei* ST11). Additionally, the unfermented, pH-unadjusted base was evaluated. For *S. thermophilus* ST496 additionally the sample after 4.5 hours fermentation was evaluated, as the pH of the end of fermentation sample was quite low.

The samples fermented with *S. thermophilus* for 4.5 h or fermented with *L. lactis* had a pleasant sweet yogurt like taste with no powdery/sandy mouthfeel or aftertaste, while the unfermented mix had a neutral taste and a slightly powdery/sandy mouthfeel.

The other fermented samples were somewhat inferior in taste. After considering the tasting, the most promising strains are *S. thermophilus* ST496 and *L. lactis* NCC 2415.

Conclusions

It has been shown that it is possible to ferment a potato protein (high molecular mass fraction) based formula with *S. thermophilus* ST496 equally as well as a milk-based formula. A pleasantly fresh yogurt like smell and taste could be achieved for the potato based formula by fermentation.

A low molecular mass potato protein fraction was found to be a better choice than a high molecular mass fraction due to its lower viscosity, milk-like appearance and non-powdery mouth feel. Fermentation of this formula with either *S. thermophilus* ST496 or *L. lactis* NCC 2415 led to a pleasant yogurt like taste and smell.

All publications mentioned in the above specification are herein incorporated by reference. Various modifications and variations of the described compositions, methods and uses of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A nutritional composition produced by fermenting a mixture comprising protein, carbohydrate and fat, wherein the major source of the protein in the mixture is potato protein, the mixture is fermented by lactic acid-producing bacteria selected from the group consisting of *Streptococcus salivarius* subsp. *thermophilus*, *Lactococcus lactis*, *Bifidobacterium longum*, and mixtures thereof, and the nutritional composition does not comprise any dairy protein.

2. The nutritional composition of claim 1, wherein the potato protein is at least about 75% by weight of a total amount of the protein in the nutritional composition.

3. The nutritional composition of claim 1, wherein the lactic acid-producing bacteria are selected from the group consisting of *Streptococcus thermophilus* ST496, *Lactococcus lactis* NCC 2415 and *Bifidobacterium longum* BL999.

4. The nutritional composition of claim 1, wherein the lactic acid-producing bacteria comprise *Streptococcus thermophilus* ST496.

5. The nutritional composition of claim 1, wherein the nutritional composition is an infant formula or a potato protein-based yogurt.

6. The nutritional composition of claim 5, wherein the infant formula is in the form of a powder or a liquid.

7. The nutritional composition of claim 5, wherein the infant formula is in the form of a reconstituted infant formula.

8. The nutritional composition of claim 1, wherein the nutritional composition is an infant formula comprising:

(a) 1.8 g-3.2 g protein per 100 kcal of the nutritional composition;
(b) 9 g-14 g carbohydrate per 100 kcal of the nutritional composition; and
(c) 4.0 g-6.0 g lipids per 100 kcal of the nutritional composition.

9. A method for producing the nutritional composition of claim 1, the method comprising:
   (a) providing a solution comprising the protein, the carbohydrate and the fat, wherein the major source of the protein in the solution is the potato protein;
   (b) adding lactic acid-producing bacteria to the solution of step (a); and
   (c) fermenting the solution of step (b) to form the nutritional composition.

10. The method of claim 9, wherein the fermenting of step (c) is performed for about 4 hours-10 hours at a temperature of about 20° C.-45° C.

11. The method of claim 9, wherein the fermenting of step (c) is continued until the solution of step (b) reaches a pH of about 3.8-about 5.5.

12. The method of claim 9, wherein the fermenting of step (c) is performed at a temperature of about 30° C.-45° C.

13. The method of claim 9, wherein the fermenting of step (c) is continued until the solution of step (b) reaches a pH of about 4.8-about 5.2.

14. The nutritional composition of claim 1, wherein an additional source of the protein is a plant protein selected from the group consisting of pea protein, rice protein, quinoa protein, oat protein, sunflower protein, coconut protein, and combinations thereof.

15. The nutritional composition of claim 1, wherein the lactic acid-producing bacteria are either *Streptococcus salivarius* subsp. *thermophilus* or *Lactococcus lactis*.

16. The nutritional composition of claim 1, wherein the lactic acid-producing bacteria are either *Streptococcus thermophilus* ST496 or *Lactococcus lactis* NCC 2415.

17. The nutritional composition of claim 1, wherein the remaining source of the protein is a plant protein.

* * * * *